US006620612B1

(12) United States Patent
Bertling

(10) Patent No.: US 6,620,612 B1
(45) Date of Patent: Sep. 16, 2003

(54) DEVICE FOR CONDUCTING BIOCHEMICAL AND MICROBIOLOGICAL REACTIONS

(75) Inventor: Wolf Bertling, Erlangen (DE)

(73) Assignee: November Aktiengesellschaft Gesellschaft fur Molekulare Medizin, Erlangen (DE)

( * ) Notice: Subject to any disclaimer, the term of this patent is extended or adjusted under 35 U.S.C. 154(b) by 0 days.

(21) Appl. No.: 09/807,715

(22) PCT Filed: Oct. 19, 1999

(86) PCT No.: PCT/DE99/03351

§ 371 (c)(1), (2), (4) Date: Apr. 17, 2001

(87) PCT Pub. No.: WO00/23189

PCT Pub. Date: Apr. 27, 2000

(51) Int. Cl.[7] .................................................. C12M 1/34

(52) U.S. Cl. ................................ 435/287.2; 435/287.3; 435/288.3; 435/288.4; 435/288.7

(58) Field of Search ........................... 435/287.1, 287.2, 435/287.3, 288.3, 288.4, 288.7

(56) References Cited

U.S. PATENT DOCUMENTS 4,599,314 A 7/1986 Shami
5,126,276 A 6/1992 Fish et al.
6,448,066 B1 * 9/2002 Wheatcroft .............. 435/287.2
6,458,582 B1 * 10/2002 Kimura et al. ........... 435/286.2

FOREIGN PATENT DOCUMENTS

WO WO 93/20240 10/1993
WO WO 96/02836 2/1996

* cited by examiner

*Primary Examiner*—David A. Redding
(74) *Attorney, Agent, or Firm*—Rankin, Hill, Porter & Clark LLP

(57) ABSTRACT

The invention relates to a device for conducting biochemical and microbiological reactions, comprising a support (2) for receiving at least one reaction vessel (3) and a device (5) for pressing a closing means (11, 12) sealing the reaction vessel (3), wherein the closing means (11, 12) project in closed position in the area surrounded by the reaction vessel (3). According to the invention, in order to accelerate and simplify reaction, an inner wall of the closing means opposite the reaction vessel (3) is coated with a molecule (14) on which a molecule to be detected can be bonded or deposited, wherein the molecule (14) contains a nucleic acid, an amino acid or a synthetic derivative of a nucleic or amino acid.

21 Claims, 4 Drawing Sheets

DEVICE FOR CONDUCTING BIOCHEMICAL AND MICROBIOLOGICAL REACTIONS

Figure 2:
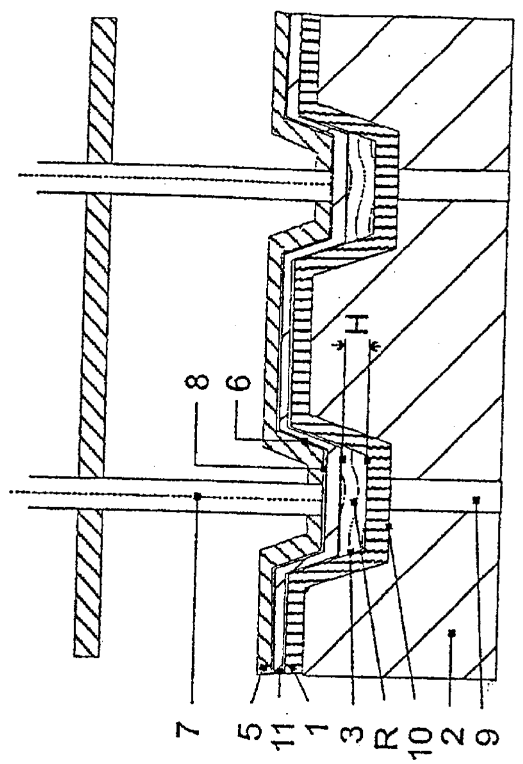

The invention relates to a device for conducting biochemical and microbiological reactions according to the preamble of claim 1.

It has been known in the art to use a microtiter plate with 96 vessels for concurrently carrying out a plurality of molecular biological reactions, such as e.g., the polymerase chain reaction (PCR). After the vessels of the microtiter plate are filled with the reaction solution, they are covered with a foil. While the PCR is being carried out, the foil is pressed against the microtiter plate by means of a heatable cover. The known method is quite time-consuming since relatively large quantities of reaction solution have to simultaneously undergo a temperature treatment that has to be accurately performed.

U.S. Pat. No. 5,455,175 shows a so-called thermocycler that permits to repeatedly expose a plurality of liquid biological samples to a predetermined temperature profile for carrying out PCR. In order to shorten the time required for temperature treatment, a small volume of biological samples at a time is accepted in a thin-walled glass capillary tube. For this purpose, each sample must be filled individually into the capillary tube and then welded. Sample preparation is time-consuming.

The generic DE-OS 44 12 281 A1 describes a system for carrying out reaction processes in a contamination-free fashion. The system includes reaction vessels, individual lids for the reaction vessels and a device for automatically opening the individual lids. In a closed position, the lid projects into the space surrounded by the reaction vessel. This enables the device to engage and, as a result thereof, the individual lids to open automatically.

U.S. Pat. No. 4,599,314 discloses a support into which a plurality of reaction vessels may be inserted. The covers intended to close the reaction vessels may be jointly lifted off the reaction vessels by means of a plate provided with an adhesive tape. The time required for carrying out the reactions is not substantially reduced thereby.

It is the object of the present invention to overcome the prior art disadvantages. More specifically, it aims at more specifically indicating a device that makes it possible to concurrently carry out a plurality of biochemical or microbiological reactions with little time expenditure.

This object is achieved by the features of claim 1. Appropriate embodiments will arise out of the features of the claims 2 to 21.

According to the invention, there is provided that an inner side of the closing means that faces the reaction vessel is coated with a molecule on which a molecule to be detected can be bonded or deposited, wherein the molecule contains a nucleic acid, an amino acid or a synthetic derivative of a nucleic or amino acid.

The molecule may be a nucleic acid probe, a gene, a peptide, protein, PNA (=peptide nucleic acid), PTO (phosphorothioate) or the like. When using a nucleic acid probe, the bonding and depositing capacity of the molecule to be detected consists in hybridization with a nucleic acid that is complementary to the nucleic acid probe. In case a peptide or a protein is used as a molecule, an antigen/antibody bond may form with the molecule to be detected. The molecule has the property to specifically bond to the molecule to be detected.

The device according to the invention permits to carry out microbiological reactions in a particularly quick and efficient way. Since the closing means projects into the space surrounded by the reaction vessel, only small volumes of sample are required. A therein potentially contained molecule to be detected may be quickly and efficiently amplified by means of PCR for example.

The closing means of preference is a cover made of synthetic material and is preferably transparent. Such a cover is inexpensive. It may be designed as a one-way product.

The pressing device may be provided with a projection that conforms to the shape of the cavity. The cavity is thus readily sealed.

The closing means may also be a foil that is made of a synthetic material, is flexible and preferably transparent. The foil serves to further seal a cavity closed by a projection.

According to another feature of the embodiment, the pressing device is provided with a location facility for the cover(s). As a result thereof, the cover(s) may be placed automatically.

The location facility may be appropriately designed as a tube or a rod for frictional engagement of a separate cover. A facility for removably fastening the cover may also be provided in the vicinity of the free end of the tube or rod. It may be an U-shaped profile that projects radially outward, one of its legs being connected to the tube and the other leg being shorter than the one leg. Such a facility readily allows the location of a cover. For this purpose, the cover is appropriately provided with an outward projecting rim that corresponds to the U-shaped profile. The rim and the matching U-shaped profile advantageously extend over two peripheral sections of about 90°. The location element may be rotatable about approximately 90°. By using the embodiment of the rim and of the matching U-shaped profile as they have been described herein above, a simple location of the cover may be achieved by way of such a rotation.

Each location element may additionally be axially movable. This allows to press on and take off certain covers separately.

According to a further embodiment, a throwing off element may be provided, said throwing off element coaxially surrounding the location element and being movable relative to said location element. This allows covers that are, e.g., held on the location element by frictional engagement to be thrown off.

The covers may of course not only be held on the location facility by frictional engagement, they may also be fastened to it by means of a releasable snap connection. For this purpose, a location facility designed as a rod or a tube may be provided on its outer periphery with a radially contouring bulge that cooperates with a corresponding groove on the inner wall of the cover.

Advantageously, there is provided between a plurality of location elements at least one punch that is movable relative to the location elements. This facilitates the simultaneous release of several covers.

It is deemed particularly advantageous to have the projection, the tube or the rod provided with optical waveguides for introducing light into or for observing light produced in the cavity, respectively. The optical waveguides may be connected to a source of light and/or to a facility for detecting fluorescence. This allows to conduct the procedure in a particularly rapid and efficient manner.

Advantageously, a plurality of reaction vessels are provided and the reaction vessels are part of a microtiter plate. Reaction vessels designed in such a way may be employed, e.g. in conventional thermocyclers for carrying out PCR. When the reaction vessels are thus formed, a plurality of covers may be part of a cover plate. This facilitates closing and opening.

It is deemed particularly advantageous to have the cover, at least in the zone of the coating, made of an electrically conductive synthetic material, preferably of an electrically conductive polycarbonate. Such an electrically conductive polycarbonate may be made by adding graphite or graphite fibers, respectively. Intrinsically conductive synthetic materials such as polyaneline, or polyacetylene may also be utilized, though. The electrically conductive zone may be contacted. As a result thereof it is possible to, e.g., apply a potential over the sample solution and to cause the charged molecules to be detected that are contained in the sample to move in the direction of the coating. It is however also possible to prove bonding or deposition of the molecules to be detected to the molecule of the coating by means of voltammetric methods.

Exemplary embodiments of the invention are described hereinafter in more detail with the help of the drawing.

Figure 1:
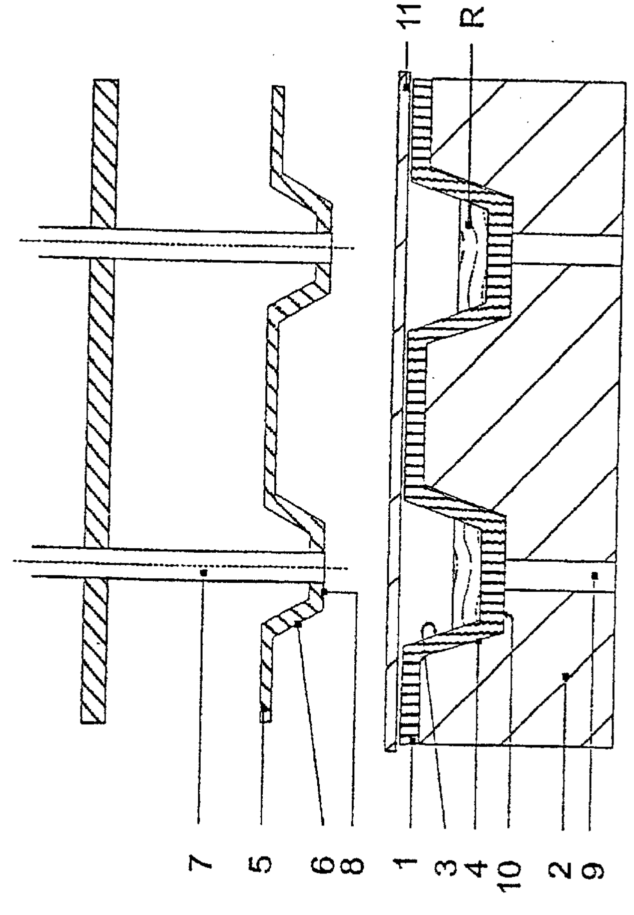
Figure 4:
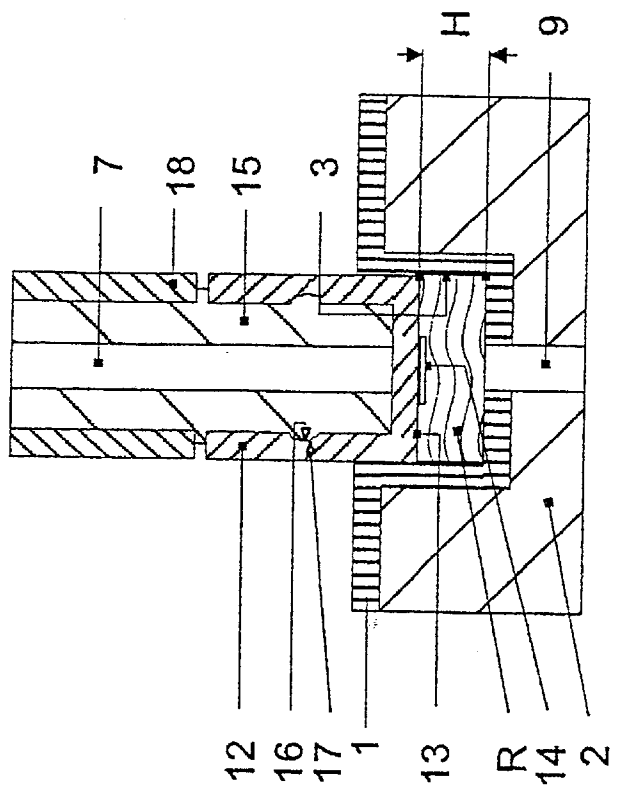
Figure 3:
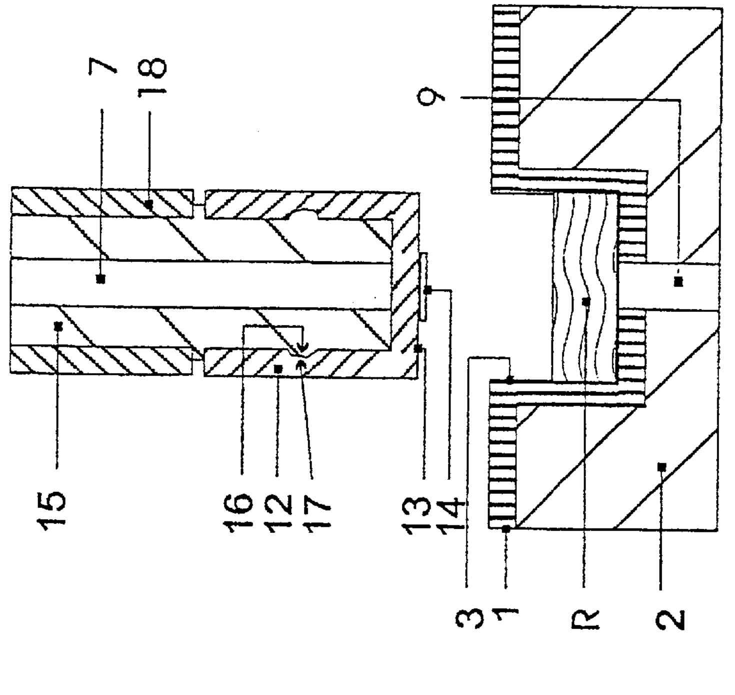
Figure 5:
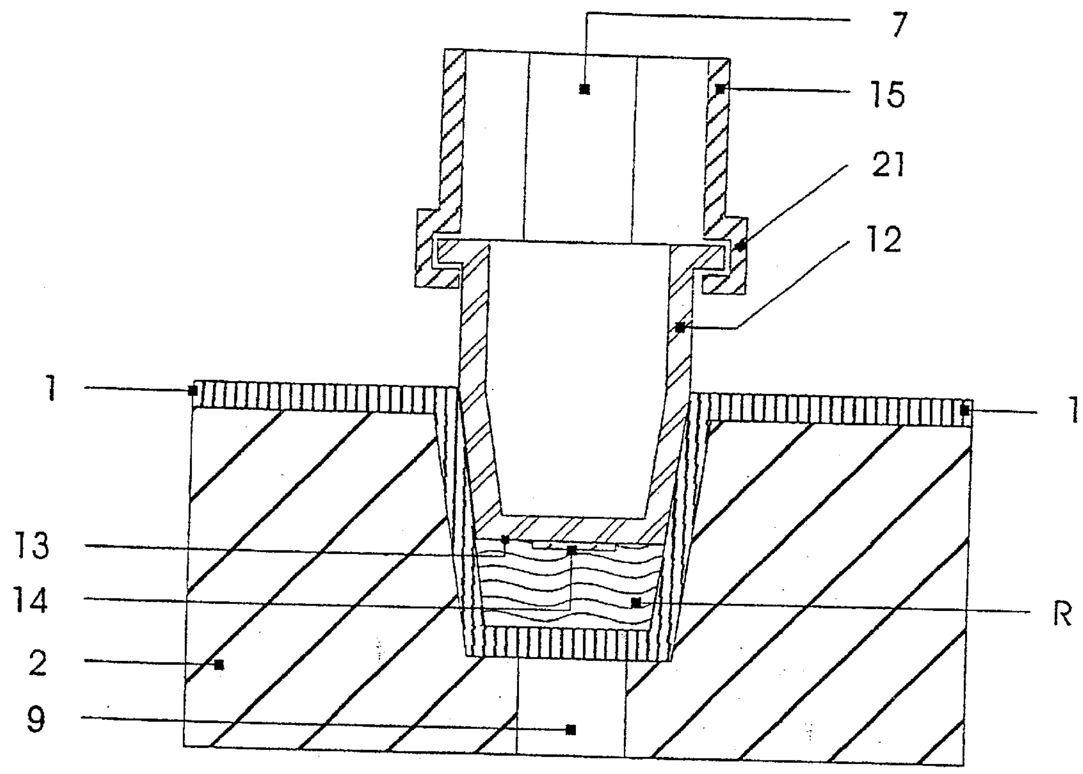
Figure 6:
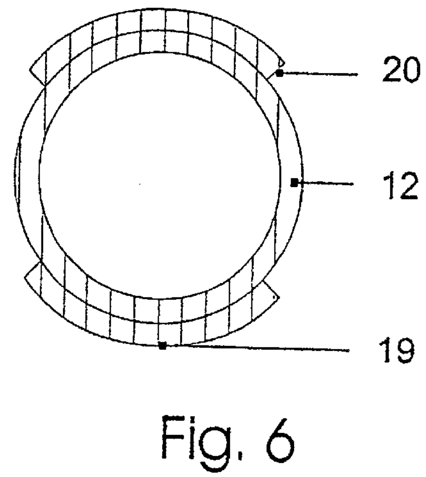
Figure 8:
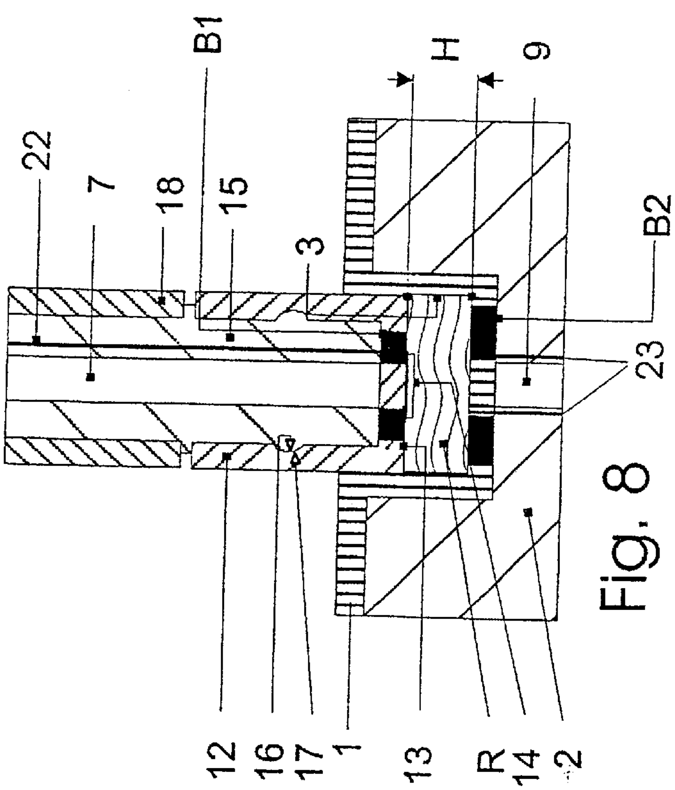
Figure 7:
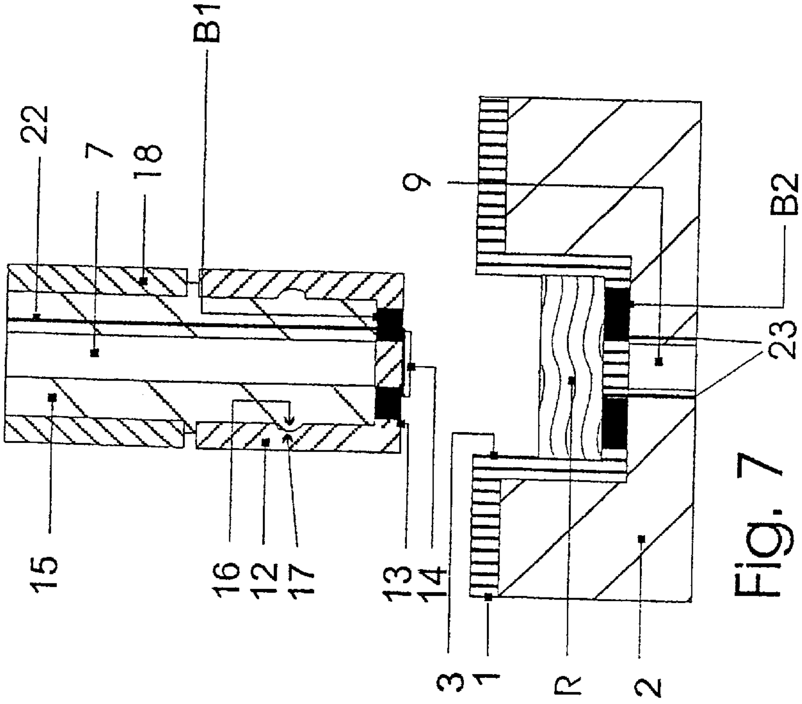

FIG. 1 is a schematic cross sectioned view of a first exemplary embodiment in a first position, FIG. 2 is the cross sectioned view of FIG. 1 in a second position, FIG. 3 is a schematic cross sectioned view of a second exemplary embodiment in a first position, FIG. 4 is a schematic cross sectioned view of FIG. 3 in a second position, FIG. 5 is a schematic cross sectioned view of a third exemplary embodiment, FIG. 6 is a top view of a cover according to the third exemplary embodiment, FIG. 7 is a schematic cross sectioned view of a fourth exemplary embodiment in a first position and FIG. 8 is a schematic cross sectioned view according to FIG. 7 in a second position.

In the FIGS. 1 and 2, a transparent microtiter plate 1 which is preferably made of polycarbonate is located in a support 2. Conically designed reaction vessels or cavities 3 of the microtiter plate 1 engage in matching recesses 4 in the support 2. A pressing device 5 is provided with conical projections 6 matching the opposite cavities 3. The one end of a first optical waveguide 7 is located on the projection area 8 opposite the cavity 3. The one end of a second optical waveguide 9 is situated in a bottom area 10 of the recess 4. A foil 11 made of a transparent, flexible synthetic material covers the cavities 3. A reaction solution contained in the cavities 3 is indicated at R. The foil 11 may be coated with a nucleic acid probe (not shown in the drawing herein) on the side facing the reaction solution R.

FIG. 2 shows the closed condition. The foil 11 contacts the reaction solution R and the projection area 8 is directly adjacent the foil 11. The closing means, in this case the foil 11, projects into the cavity 3. A height H amounts to approximately 0.5 to 1.5 mm. As a result thereof, it is possible to keep the reaction volume small in the way of a capillary slot and to respectively heat or cool the reaction solution R by means of a heating and cooling facility provided in the support 2 and in the pressing device 5 (not shown herein).

The FIGS. 3 and 4 show a second exemplary embodiment in which the cavity 3 has got a cylindrical shape. Here, each cavity 3 is provided with a separate cover 12 serving as a closing means. A nucleic acid probe 14 is located on the underside 13 of the cover, said underside opposing the cavity. The cover 12 is located on a location element designed as a tube 15. A bulge 16, which is provided on the tube 15 and surrounds it, engages in an annular groove 17 on an inner wall of the cover 12. The first optical waveguide 7 is located in the tube 15. The tube 15 is coaxially surrounded by another tube 18. The other tube 18 is axially movable. FIG. 4 shows the closing position. The underside 13 of the cover is in contact with the reaction solution R.

In the third exemplary embodiment shown in the FIGS. 5 and 6, the cover 12 has again a substantially cylindrical shape and is provided with a nucleic acid probe on the underside 13 of the cover.

The cover is provided with two radial rim projections 19 designed as annular segments, each of them being fitted at its one end with an axially running injection-molded stop 20. Two partially contouring U-shaped profiles 21 are provided at the end of the tube 15 for engagement with the rim projections 19.

FIGS. 7 and 8 show a fourth embodiment. Here, the cover 12 is in parts made of an electrically conductive synthetic material. The conductive zones B1, B2 are designed as tube sections that surround a transparent zone located between the end of the first optical waveguide and the nucleic acid probe 14 in a case-like fashion. The electrically conductive first zone B1 is provided with a contact (not shown) at the end of a first line 22 incorporated in the tube 15. The contact is pressed against the first electrically conductive zone B1 on placing the cover 12 onto the tube 15. Likewise, a tubular second electrically conductive zone B2 that is filled with a transparent synthetic material is also provided in the bottom of the cavity 3 of the microtiter plate 1. An electrically conductive connection is established between the second electrically conductive zone B2 and a second line 23.

The function of the devices is as follows:

First, a predetermined quantity of reaction solution R is pipetted into the cavities 3.

According to the first embodiment, the cavities 3 are covered with the foil 11 which is coated on its side facing the reaction solution with a nucleic acid probe (not shown). Then, the projections 6 are moved toward the cavities 3 until the foil 11 projects into the cavity 3 and the coating directly contacts the reaction solution R. In order to make certain of sufficient tightness, the projections 6 are pressed against the microtiter plate 1 while the reaction is taking place.

In the second, third and fourth embodiment, a nucleic acid probe 14 is provided on the underside of the cover 12 that faces the reaction solution. The nucleic acid probe 14 is brought into contact with the reaction solution R.

The cover 12 which is made at least in parts of a transparent synthetic material may be held on an axially movable tube 15 by means of a snap-in connection 16, 17 or by means of frictional engagement. The cover 12 is brought to the closing position shown in the FIGS. 4 and 8 by axially moving the tube 15. To open the cavity 3, the cover 12 is lifted by axially moving the tube 15 in the opposite direction. It may then be thrown off by axially moving the other tube 18.

In the third embodiment represented in the FIGS. 5 and 6, the tube 15, with the U-shaped profiles 21 provided at the end of said tube, axially enters the gaps of the cover 12 formed between the rim projections 19. By rotating the U-shaped profiles 21 about approximately 90°, they are brought to a position in which they encompass the rim projections 19. The stops 20 make certain that the cover 12 correctly fits on the tube 15. To release the cover 12, the sequence is reversed.

The support may be part of a thermocycler for carrying out PCR. For conducting a biochemical identification reaction, a reaction solution R containing the molecule to be detected is pipetted into each cavity 3 of a microtiter plate. Each cavity 3 is closed by means of a cover 12. The covers 12 advantageously are component part of a cover plate which is made in one piece. Each cover 12 is coated on the inner side facing the reaction solution R with another nucleic acid probe.

The microtiter plate which has been closed with the cover plate is then placed into the support 2. The support 2 is heated and cooled in cycles. PCR ensues, by means of which a molecule to be detected which is contained in the reaction solution R is amplified.

The molecule bonds to the corresponding nucleic acid probe 14. In case it bonds to the nucleic acid probe 14, it may be detected by means of fluorescence. For this purpose, the fluorescence radiation that may occur is transmitted by means of the first 7 and/or the second optical waveguide 9 to a detector where it is analyzed.

In the fourth exemplary embodiment, an additional potential may be applied over the reaction solution R by applying a voltage over the electrically conductive zones provided in the cover 12 and in the bottom of the cavity in order to accelerate deposition of the molecule to be detected on the nucleic acid probe 14. In so doing, negatively charged molecules of, e.g. nucleic acid may be moved toward the nucleic acid probe 14 and be enriched there.

It is also possible though to detect a bond of nucleic acids or molecules to be detected to the nucleic acid probe 14 or to the molecular coating respectively by means of the electrically conductive zones or electrodes respectively, e.g., by means of voltammetric methods.

It is also possible to have the covers 12 made of an electrically conductive synthetic material in only the first zone B1 of the molecular coating or to have an electrode made of metal, preferably of gold, incorporated in this zone. The electrically conductive zone B1, B2 may be surrounded by a zone made of an insulating synthetic material. In this case, the electrically conductive zone B1, B2 forms an electrode that is in contact with the molecular coating. In the event that a plurality of covers 12 are provided in the form of a cover plate, each cover 12 is provided in this case with a separate electrode. By means of the electrodes it is possible to simultaneously measure a change in potential at each cover 12.

The optical waveguides 7, 9 make it possible to radiate ultraviolet light for example and/or, alternatively, to detect a fluorescence occurring in the reaction solution R. This also permits to detect the presence of the molecule to be detected in the reaction solution R.

Punches (not shown in the drawing herein) may be provided between the tubes 15. On removing the covers 12, the punches may be moved toward the microtiter plate 1 and may keep it in its position on the support 2.

Listing of Numerals 1 microtiter plate
2 support
3 cavity
4 recess
5 pressing device
6 projection
7 first optical waveguide
8 projection area
9 second optical waveguide
10 bottom area
11 foil
12 cover
13 underside of the cover
14 nucleic acid probe
15 tube
16 bulge
17 annular groove
18 further tube
19 rim projections
20 stop
21 U-shaped profile
R reaction solution
H height
B1 first zone
B2 second zone

What is claimed is:

1. A device for conducting biochemical and microbiological reactions comprising a support (2) for receiving at least one reaction vessel (3) and a device (5) for pressing a closing means (11, 12) sealing the reaction vessel (3), the closing means (11, 12) projecting in its closed position in the space surrounded by the reaction vessel (3), an inner wall of the closing means that faces the reaction vessel (3) being coated with a molecule (14) on which a molecule to be detected can be bonded or deposited, the molecule containing a nucleic acid, an amino acid or a synthetic derivative of a nucleic or amino acid, wherein the closing means (12), at least in the zone of the coating, is made of an electrically conductive synthetic material.

2. The device according to claim 1 wherein the closing means (11, 12) is a cover (12) made of transparent synthetic material.

3. The device according to claim 1, wherein the pressing device (5, 15) is provided with a projection (6) that conforms to the shape of the reaction vessel (3).

4. The device according to claim 1, wherein the pressing device (5) is provided with a location element for the cover (12).

5. The device according to claim 4, wherein the location element is designed as a tube (15) or a rod.

6. The device according to claim 5, wherein an element for removably fastening the cover (12) is provided in a vicinity of a free end of the tube (15) or rod.

7. The device according to claim 6, wherein the element for removably fastening the cover (12) is provided with an U-shaped profile (21) that projects radially outward, one of its legs being connected to the tube (15) and the other leg being relatively shorter than the one leg.

8. The device according to claim 7, wherein the cover (12) is provided with an outward projecting rim (19) that corresponds to the U-shaped profile (21).

9. The device according to claim 8, wherein the rim (19) and the U-shaped profile (21) each extend over two peripheral sections of about 90°.

10. The device according to claim 5, wherein the location element is rotatable about approximately 90°.

11. The device according to claim 5, wherein the location element is axially movable.

12. The device according to claim 5, further comprising a throwing off element (18,) said throwing off element coaxially surrounding the location element and being movable relative to said location element.

13. The device according to claim 4, wherein the location element is designed as a rod or a tube (15) and is provided on its outer periphery with a radially contouring bulge (16) that cooperates with a corresponding groove on the inner wall of the cover (12).

14. The device according to claim 13, wherein there is provided between a plurality of location elements at least one punch that is movable relative to the location elements.

15. The device according to claim 1, wherein the pressing device includes a projection and location element, said projection conforming to the shape of the reaction vessel and said location element being a rod or tube for locating the cover, and wherein at least one of said projection and said tube or rod includes optical waveguides (7, 9) for introducing light into or for observing light produced in the cavity (3), respectively.

16. The device according to claim 15, wherein the optical waveguides (7, 9) are connected to a source of light.

17. The device according to claim 15, wherein the optical waveguides (7, 9) are connected to an element for detecting fluorescence.

18. The device according to claim 1, wherein a plurality of reaction vessels (3) are provided and the reaction vessels are part of a microtiter plate.

19. The device according to claim 18, wherein a plurality of covers (3) are part of a cover plate.

20. The device according to claim 1, wherein the electrically conductive synthetic material is an electrically conductive polycarbonate.

21. The device according to claim 1, wherein the electrically conductive zone is contacted.

* * * * *

UNITED STATES PATENT AND TRADEMARK OFFICE

CERTIFICATE OF CORRECTION

PATENT NO. : 6,620,612 B1
APPLICATION NO. : 09/807715
DATED : September 16, 2003
INVENTOR(S) : Bertling It is certified that error appears in the above-identified patent and that said Letters Patent is hereby corrected as shown below:

On the Title Page, insert --Section [30], Foreign Application Priority Data, October 21, 1998, (DE).......198 48 515.8--.

Signed and Sealed this

Thirty-first Day of July, 2007

JON W. DUDAS
*Director of the United States Patent and Trademark Office*